US006274345B1

(12) United States Patent
Lee et al.

(10) Patent No.: US 6,274,345 B1
(45) Date of Patent: Aug. 14, 2001

(54) **EXPRESSION VECTORS ENCODING *ESCHERICHIA COLI* OMPC AS A CELL SURFACE ANCHORING MOTIF**

(75) Inventors: Sang Yup Lee, Teajon; Zhaohui Xu, Taejon; Jong Hyun Choi, Seoul, all of (KR)

(73) Assignee: Korea Advanced Institute of Science and Technology, Teajon (KR)

( * ) Notice: Subject to any disclaimer, the term of this patent is extended or adjusted under 35 U.S.C. 154(b) by 0 days.

(21) Appl. No.: 09/507,323

(22) Filed: Feb. 18, 2000

(30) Foreign Application Priority Data

Feb. 22, 1999 (KR) ............................................. 99-0005773

(51) Int. Cl.⁷ ........................... C12N 15/00; C12N 15/70; C12N 1/20; C12P 21/06; C07H 21/04
(52) U.S. Cl. ...................... 435/69.7; 435/69.1; 435/69.8; 435/243; 435/252.3; 536/23.4; 536/23.1
(58) Field of Search ................................. 536/23.1, 23.4; 435/69.1, 69.7, 471, 320.1, 69.8, 243, 252.3

(56) References Cited

U.S. PATENT DOCUMENTS 5,356,797 10/1994 Nielsel et al. .

FOREIGN PATENT DOCUMENTS

WO 97/09437  3/1997 (WO) .
WO 98/49286  11/1998 (WO) .

OTHER PUBLICATIONS

Mizuno et al. Mol. Gen. Genet. 207:217–223, 1987.*
Marja Agterberg et al., Outer–membrane PhoE protein of *Escherichia coli* K–12 as an exposure vector: possibilities and limitations. *Gene* 88, 1990, pp. 37–45.
Linda A. Egger et al., Signal Transduction via the histidyl–aspartyl phospho–relay, *Genes to Cells*, 2, 1997, pp. 167–184.
George Georgiou et al., Display of heterologous proteins on the surface of microorganisms: From the screening of combinatorial libraries to live recombinant vaccines, *Nature Biotechnology*, vol. 15, Jan. 1997, pp. 29–34.
George Georgiou et al., Practical applications of engineering Gram–negative bacterial cell surfaces, *Tibtech*, vol. 11, Jan. 1993, pp. 6–10.
Heung–Chae Jung et al., Expression of carboxymethylcellulase on the surface of *Escherichia coli* using *Pseudomonas syringae* ice nucleation protein, *Enzyme and Microbial Technoloby*, 22, 1998, pp. 248–354.

Zhijian Lu et al., Expression of Thioredoxin Random Peptide Libraries on the *Escherichia coli* Cell Surface as Functional Fusions to Flagellin: A System Designed for Exploring Protein–Protein Interactions, *Bio/Technology*, vol. 13, Apr. 1995, pp. 366–372.
Thien Ngoc Nguyen et al., Cell–surface display of heterologous epitopes on *Staphylococcus xylosus* as a potential delivery system for oral vaccination, *Gene*, 128, 1993, pp. 89–94.
Jose Luis Puente, The *Salmonella ompC* gene: structure and use as a carrier for heterologous sequences, *Gene*, 156, 1995, pp. 1–9.
Carolina Sousa et al., Enhanced metalloadsorption of bacterial cells displaying poly–His peptides, *Nature Biotechnology*, vol. 14, Aug. 1996, pp. 1017–1020.
Carolina Sousa et al., Metalloadsorption by *Escherichia coli* Cells Displaying Yeast and Mammalian Metallothioneins Anchored to the Outer Membrane Protein LamB, *Journal of Bacteriology*, vol. 180, No. 9, May 1998, pp. 2280–2284.
Stefan Stahl et al., Bacterial surface display: trends and progress, *Iibtech*, vol. 15, May 1997, pp. 185–192.
Andreas Strauss et al., In vivo immobilization of enzymatically active polypeptides on the cell surface of *Staphylococcus carnosus*, *Molecular Microbiology*, 21(3), 1996, pp. 491–497.

\* cited by examiner

*Primary Examiner*—Robert A. Schwartzman
*Assistant Examiner*—Gerald G. Leffers, Jr.
(74) *Attorney, Agent, or Firm*—Knobbes, Martens, Olson & Bear, LLP

(57) ABSTRACT

The present invention relates to expression vectors containing a gene encoding outer membrane protein C(OmpC) from *Escherichia coli* as a cell surface anchoring motif, more specifically, to expression vectors comprising a gene encoding OmpC which is designed to express a gene of foreign protein in fused form with OmpC on the cell surface of *Escherichia coli*, and a method for displaying the desired protein on the surface of the bacteria employing the OmpC as a cell surface anchoring motif. In accordance with the present invention, the desired protein can be expressed efficiently on the cell surface of bacteria so that the expressed protein can be applied to a variety of applications such as live vaccine development, peptide libraries screening, antibody production, environmental bioadsorbent, whole cell catalysis, and biosensor development.

25 Claims, 11 Drawing Sheets

EXPRESSION VECTORS ENCODING ESCHERICHIA COLI OMPC AS A CELL SURFACE ANCHORING MOTIF

FIELD OF THE INVENTION

The present invention relates to expression vectors comprising a gene encoding outer membrane protein C("OmpC") from *Escherichia coli* (("*E. coli*") as a cell surface anchoring motif, more specifically, to expression vectors comprising a gene encoding OmpC which is designed to express a gene of foreign protein in fused form with OmpC on the cell surface of *E. coli*, and a method for displaying the desired protein on the surface of *E. coli* employing the OmpC as a cell surface anchoring motif.

BACKGROUND OF THE INVENTION

Bacteria have played a crucial role in the development of the biotechnology. Since the development of recombinant DNA technology, genetically engineered bacteria have been employed for the production of various recombinant proteins. Also, recombinant bacteria have been developed and used for a wide range of industrial applications such as biodegradable plastics production, heavy metal removal, sulfur removal, waste treatment, and food processing.

Recently, new advances in molecular biology and secretory expression of proteins made it possible to express foreign proteins at the outer surface of microorganisms by the technology called cell surface display.

Since the first development of surface-expression system by George P. Smith in the mid 1980 by expressing peptides or small proteins fused with pIII of the filamentous phage (see: Smith, G. P., Science, 228:1315–1317, 1985), various mechanisms of protein secretion in microorganisms have been extensively studied to develop new and better cell surface display systems by which proteins of interest can be expressed on the surface of the microorganisms. Cell surface display is a relatively new technology expressing proteins or peptides on the surface of the cell in a stable manner using the surface protein of bacteria, yeast, or even mammalian cells as a surface anchoring motif.

Before the cell surface display system was developed, phage system was used to express foreign protein on the surface of the phage, because the structure of the phage coat is simpler than that of bacteria. However, the size of foreign protein to be expressed on the surface of phage was limited. Therefore, the application of the phage surface display system has been limited. This is why new focus has been given to bacterial cell surface display system.

Gram-negative bacteria possess unique as well as complex cell envelope structure which consists of inner cellular membrane, periplasm, and outer cellular membrane. Therefore, surface anchoring motif is needed to efficiently transport foreign protein to the surface of the bacteria. For the expression of foreign proteins or peptides using the surface protein of the bacteria, appropriate bacterial surface protein has to be fused to the foreign protein of interest at the genetic level, and the expressed fusion protein has to be transported through the inner cellular membrane and outer membrane to the surface and be maintained on the surface of the bacteria.

Successful candidates for surface anchoring motif should have the following characteristics: The surface protein to be used as an anchoring motif should have efficient secretion signal sequences for facilitating the penetration of the foreign protein through the inner membrane of the cell, targeting signal for anchoring foreign protein to the surface of the cell in a stable manner, and capacity to accommodate foreign proteins or peptides of various sizes. Furthermore, it would be beneficial if the fusion protein can be expressed in large amounts.

A variety of cell surface display systems have been developed to date, which may be classified into three groups according to their recombinant profiles: C-terminal fusion, N-terminal fusion, and sandwich fusion. If a native surface protein has a discrete localization signal within its N-terminal portion, a C-terminal fusion strategy may be considered to fuse the foreign peptides to the C-terminal of that function portion. The Lpp-OmpA motif developed in *E. coli* is a good example of C-terminal fusion system (see: Georgiou, G., et al., Protein Eng., 9:239–247, 1996). Similarly, N-terminal fusion systems have been developed using *Staphylococcus aureus* protein A (see: Gunneriusson, E., et al., J. Bacteriol., 178:1341–1346, 1996), *Staphylococcus aureus* fibronectin binding protein B (see: Strauss, A., et al., Mol. Microbiol., 21:491–500, 1996), and *Streptococcus pyogenes* fibrillar M protein (see: Pozzi, G., et al., Infect. Immun., 60:1902–1907, 1992), all of which contain C-terminal sorting signals to target foreign proteins to the cell wall. However, many surface proteins do not have such anchoring regions, and thus the whole structure is required for the assembly. Therefore, a sandwich-fusion system in which a foreign protein of interest is inserted into the surface protein has also been developed. Several examples employing this system include *E. coli* PhoE (see: Agterberg, M., et al., Gene, 88:37–45, 1990), FimH (see: Pallesen, L., et al., Microbiology, 141:2839–2848, 1995), and PapA (see: Steidler, L., et al., J. Bacteriol., 175:7639–7643, 1993). However, it is generally believed that the exposed loops of outer membrane proteins (OMPs) can only accept insertions of 60–70 amino acids or less (see: Georgiou, G., et al., Nature Biotechnol., 15:29–34, 1997; Stahl, S., et al., Trends Biotechnol., 15:185–192, 1997).

Under the current circumstances, there are strong reasons for exploring and developing an alternative cell surface display system to allow expression and display of foreign proteins consisted of more amino acid residues.

The cell surface display can be employed for a wide range of biotechnological and industrial applications such as:

(1) Live vaccine development—to expose heterologous epitopes on human commensal or attenuated pathogenic bacterial cells to elicit antigen-specific antibody responses (see: Nguyen, T. N., et al., Gene, 128:89-94, 1993);

(2) Peptide libraries screening—to screen displayed peptide libraries by sequential binding and elution, or more efficiently, by fluorescence-activated cell sorting (see: Francisco, J. A., et al., Proc. Natl. Acad. Sci., USA., 90:10444–10448, 1993; Georgiou, G., WO9849286, 1998);

(3) Antibody production—to express surface antigens to raise polyclonal antibodies in animal (see: Charbit, A., et al., Gene, 70:181–189, 1988);

(4) Environmental bioadsorbents—to modify cell surface for the removal of harmful chemicals and heavymetals (see: Sousa, C., et al., J. Bacteriol., 180:2280–2284, 1998);

(5) Whole cell catalysts—to immobilize enzymes on the outmost layer of cells to catalyze biochemical reactions directly (see: Richins, R. D., et al., Nature Biotechnol., 15:984–987, 1997); and, (6) Biosensor development—to anchor enzymes, receptors, or other signal-sensitive components on cell surface to develop novel biosensors for diagnostic, industrial or environmental purposes.

SUMMARY OF THE INVENTION

The present inventors have made an effort to develop a novel cell surface display system to allow expression of larger foreign proteins/peptides by employing outer membrane protein C(OmpC) of *E. coli* as a cell surface anchoring motif, and found that recombinant proteins can be expressed efficiently on the cell surface of recombinant *E. coli* transformed with a novel expression vector containing a gene encoding OmpC. In particular, they found that a transformant harboring a recombinant plasmid vector expressing poly-histidine linker peptide in fused form with OmpC on the cell surface of *E. coli* has outstanding potential to be used as heavy metal adsorbent.

The first object of the invention is, therefore, to provide novel expression vectors containing OmpC gene of *E. coli* as a cell surface anchoring motif to express foreign proteins on the surface of *E. coli*.

The second object of the invention is to provide recombinant *E. coli* strains that are transformed with the said expression vectors.

The third object of the invention is to provide a method for manufacturing foreign proteins/peptides on the cell surface of *E. coli*, more importantly to develop a sandwich fusion surface display system that can display proteins/peptides larger than the current limitation of ca. 60 amino acids.

The fourth object of the invention is to provide a heavy metal remover comprising a microorganism which is transformed with an expression vector containing a gene of poly-histidine linker peptide fused within the gene of OmpC derived from *E. coli*.

BRIEF DESCRIPTION OF DRAWINGS

The above and the other objects and features of the present invention will become apparent from the following descriptions given in conjunction with the accompanying drawings, in which.

DETAILED DESCRIPTION OF THE INVENTION

Figure 1:
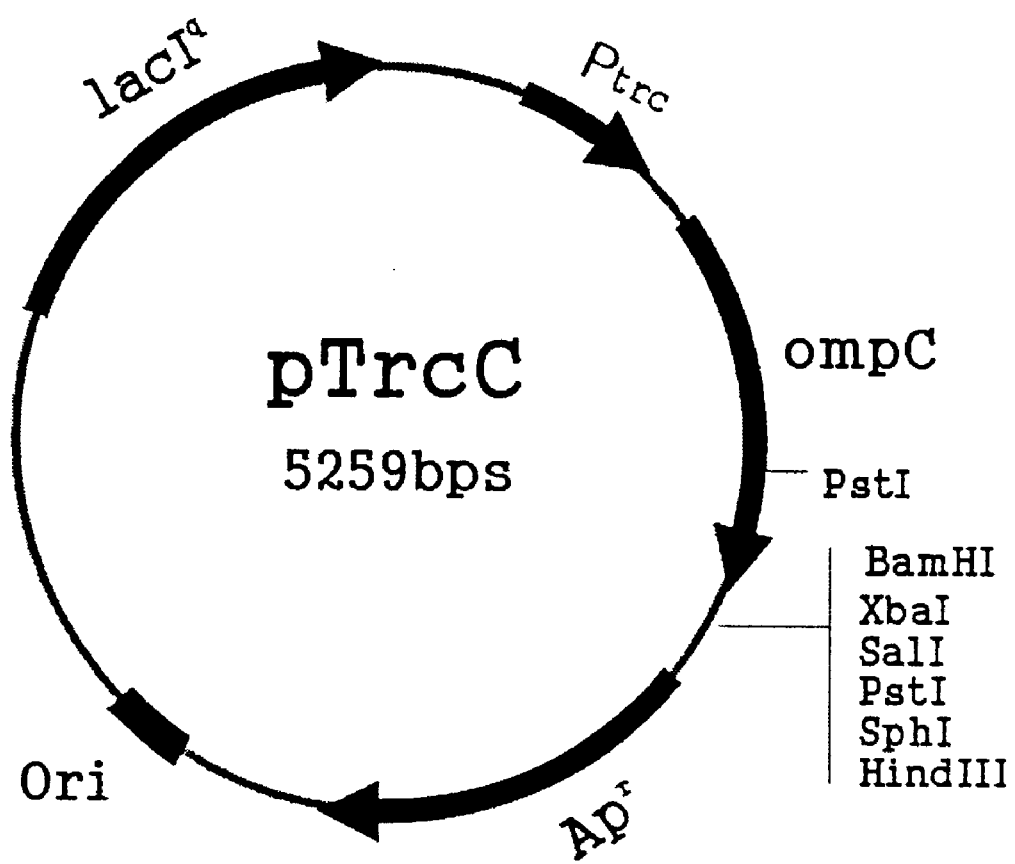
FIG. 1 shows a genetic map of plasmid pTrcC.

To establish a novel cell surface expression system, the present inventors selected the *E. coli* outer membrane protein C(OmpC) as a surface anchoring motif, which contains efficient secretion signal, and a targeting signal for stable attachment of the foreign protein on the outer membrane surface of the cell.

*E. coli* OmpC is one of the most abundant (can be up to $10^5$ molecules per cell) outer membrane proteins in *E. coli* cells. It is one of the three classical porin proteins of K-12 strains(the-other two are OmpF and PhoE) and consists of 367 amino acids including a signal peptide of 21 amino acids (see: Mizuno, T., et al., J. Biol. Chem., 258:6932–6940, 1983).

The membrane topology of OmpC derived from *Salmonella typhi* (*S. typhi*) indicated that N-terminal of OmpC is located in the periplasmic space, and there are 8 external loops outside of the outer membrane and 7 internal loops towards the periplasmic space (see: Puente, J. L., et al., Gene, 156:1–9, 1995). In the case of *S. typhi* OmpC, the $4^{th}$ and $6^{th}$ external loops, L4 and L6, have been used to display two of the rotavirus VP4 capsid protein epitopes, RV160 (22 amino acids) and RV252 (28 amino acids) (see: Puente, J. L., et al., Gene, 156:1–9, 1995).

Therefore, the present inventors first examined the conformational structure of the *E. coli* OmpC by comparing its potential structure with that of *S. typhi* OmpC, and decided to use the $7^{th}$ external loop as the point of inserting foreign protein for cell surface display.

First of all, in order to clone the *E. coli* OmpC gene, polymerase chain reaction(PCR) was performed using chromosomal DNA isolated from *E. coli* MC4100 (F-araD 139Δ (argF-lac) U169 rpsL150 (Str$^r$) relAl flbB5301 deoC1 ptsF25 rbsR; ATCC35695) as a template, and the purified DNA fragment of 1. lkb was cloned into the plasmid pTrc99A, which contains a strong inducible trc promoter (see: Amann, E., et al., Gene, 25:167–168, 1983). The resulting plasmid pTrcC expresses the *E. coli* OmpC under the control of the inducible trc promoter.

As mentioned earlier, the present inventors aimed to insert model foreign peptide into the PstI site on the $7^{th}$ external loop among the eight external loops located outside of the *E. coli* outer membrane. However, insertion of the foreign peptide into this PstI site was not straightforward because there was one additional PstI site present in the downstream of the ompC gene. Therefore, the inventors constructed a new recombinant plasmid pTCdP, in which the PstI site on the downstream region of the ompC gene is deleted. Accordingly, the recombinant plasmid pTCdP now allows easy and convenient insertion of foreign protein into the $7^{th}$ external loop of OmpC region using the PstI restriction site. The present inventors transformed *E. coli* strain MC4100 with the above expression vector pTCdP. Transformant thus prepared was designated as '*Escherichia coli* MC4100/ pTCdP', and deposited with Korean Collection for Type Cultures (KCTC, #52, Oun-dong, Yusong-ku, Taejon 305–333, Republic of Korea), an international depository authority as accession No. KCTC 0576BP on Feb. 3, 1999.

Poly-histidine (Poly-His) linker peptide comprised of 6 histidine (6His) was used as a model foreign peptide in the invention for the following two reasons: (1) it is a good chelator for bivalent metal ions, such as $Cd^{2+}$, $Cu^{2+}$, $Zn^{2+}$, $Ni^{2+}$ and $Pb^{2+}$, and therefore it can be employed as a potential bioadsorbent for heavy metal removal; and, (2) the permissive size limit of polypeptide to be fused to the external loops of OmpC can be conveniently examined by inserting varying number of copies of 6His linkers. One set of Poly-His linker (77bp) was made by PCR, and was cloned into the PstI site of recombinant plasmid pTCdP to construct a plasmid pTCHP1. The plasmid pTCHP1 contains one set of poly-His (6His) linker gene within the OmpC gene. Several recombinant expression vectors pTCHP2, pTCHP3, pTCHP6 and pTCHP12, which contain genes for 2, 3, 6 and 12 sets of poly-His linker peptide, respectively, were constructed in an analogous manner as above. The present inventors transformed *E. coli* strain MC4100 with these expression vectors. As a representative among these, the transformant harboring pTCHP6 was designated as '*Escherichia coli* MC4100/pTCHP6', and deposited with Korean Collection for Type Cultures (KCTC, #52, Oun-dong, Yusong-ku, Taejon305–333, Republic of Korea), an international depository authority as accession No. KCTC 0577BP on Feb. 3, 1999.

The expression of *E. coli* OmpC-(6His), fusion protein was examined in *E. coli* MC4100 strains harboring pTCHP1, pTCHP2, pTCHP3, pTCHP6 or pTCHP12, by inducing with IPTG(isopropyl-β-thiogalactoside). The recombinant *E. coli* stains were cultured, and the outer membrane protein fractions were analysed by SDS-PAGE. As a result, it was clearly demonstrated that the expressed OmpC-poly His fusion proteins were targeted to the *E. coli* outer membrane by using the OmpC as a surface anchoring motif. The percentage of the fusion protein expressed was high enough to reach greater than 30% of the total outer membrane proteins.

Then, in order to investigate whether the poly-His peptide was properly expressed and correctly displayed at the outer membrane of the *E. coli*, adhesion of recombinant *E. coli* cells to Nickel-nitrotriacetic acid(Ni-NTA)-agarose (Qiagen GmbH, Hilden, Germany) beads was examined. The recombinant cells displaying OmpC-(6His)$_n$ fusion proteins were attached to nickel ions on the agarose beads, which indicates that OmpC-(6His)$_n$ peptides were truly displayed at the outer surface of *E. coli* cells. Furthermore, as many as 162 amino acids(twelve sets of poly-His linker) could be displayed on the *E. coli* cell surface. Comparing with the previous results that the maximum size of foreign peptides was limited to 60 or 70 amino acids when using the sandwich fusion method (see: Georgiou, G., et al., Nature Biotechnol., 15:29–34, 1997; Stahl, S., et al., Trends Biotechnol., 15:185–192, 1997), the results of the present invention show that the *E. coli* OmpC can be employed as an efficient cell surface anchoring motif for displaying larger proteins/peptides.

Furthermore, recombinant *E. coli* MC4100 cells expressing OmpC-(6His)$_n$ fusion proteins were examined for their abilities to adsorb heavy metal ion, $Cd^{2+}$ by the aid of atomic analysis system (Perkin-Elmer 3100, U.S.A.). *E. coli* cells harboring pTCHP1, pTCHP2, pTCHP3 and pTCHP6 could adsorb 18.9, 23.9, 26.1 and 32.0 μmol of $Cd^{2+}$ per grams of cell dry weight, respectively. Accordingly, it was clearly demonstrated that the $Cd^{2+}$ removal capacity of poly-His peptides displayed using the OmpC as a cell anchoring motif was twice greater than that obtained with poly-His displayed using LamB as the anchoring motif (see: Sousa, C., et al., Nature Biotechnol., 14:1017–1020, 1996). Therefore, it was suggested that the recombinant *E. coli* cells developed in this invention may be used as an effective bioadsorbent to remove heavy metals.

During the above study, the inventors noticed that growth of the recombinant strains transformed with pTCdP, pTCHP1, pTCHP2, pTCHP3, pTCHP6, or pTCHP12 were considerably affected after induction. Since the above-mentioned plasmids use β-lactamase as the antibiotic selection marker, the secretion of β-lactamase was reasoned to affect the expression of OmpC-(6His)$_n$, and thus somewhat inhibited the growth of recombinant strains. Therefore, four more plasmids, pKCdP, pKCH3, pKCH6, and pKCH12 were constructed based on pTCdP, pTCHP3, pTCHP6, pTCHP12, respectively, by replacing the β-lactamase gene with the aminoglycoside 3'-phoshotransferase, which is a kanamycin resistance(Km$^r$) gene and encodes a non-secretory protein. The final cell densities of *E. coli* strains harboring the Km$^r$ vectors were higher than those harboring the Ap$^r$ vectors. Recombinant *E. coli* MC4100 transformed with pKCH3 and pKCH6 could adsorb 27.0 and 32.1 μmol of $Cd^{2+}$ per gram cell dry weight, respectively, which were equivalent to what have been achieved with the corresponding Ap$^r$ vectors. Therefore, *E. coli* strains harbouring Km$^r$ vectors can also display relatively large peptides/proteins without negatively affecting cell growth, which provides another practical advantage to be used as bioadsorbents. Among these, *E. coli* MC4100 transformed with pKCH6 was designated as '*Escherichia coli* MC4100/pKCH6', and deposited with the Korean Collection for Type Cultures (KCTC, #52, Oun-dong, Yusong-ku, Taejon 305–333, Republic of Korea), an international depository authority as accession No. KCTC 0653BP on Aug. 17, 1999.

The present invention is further illustrated in the following examples, which should not be taken to limit the scope of the invention. In particular, the recombinant plasmid pTCdP is a representative example of the expression vectors comprising a gene of OmpC, which can be used to display not only Poly-His linker peptide as described in the following examples, but also any foreign proteins or peptides. Therefore, any recombinant expression vectors including the recombinant plasmid pTCdP and pKCdP harboring a variety of inserted genes and the use of *E. coli* OmpC as an anchoring motif for the display of any protein/peptide on the surface of *E. coli* are also covered within the scope of this invention.

EXAMPLE 1

Construction of Recombinant Plasmid pTCdP

In order to clone the outer membrane protein C(OmpC) gene from *E. coli*, PCR was performed using chromosomal DNA isolated from *E. coli* MC4100 (F-araD 139Δ (argF-lac) U169 rpsL150 (Strr) relAl flbB5301 deoCl ptsE25 rbsR; ATCC35695) as a template. Two primers used in the reaction were 5'-CTGCGCCTACATGAAAGTTAAAGTACTG-3' (SEQ ID NO:1) containing an BsaI site(underlined) and 5'-CCGGGATCCTTATTAGAACTGGTAAACCAG-3' (SEQ ID NO:2) containing a BamHI site(underlined). The reaction mixture (100 μl) contained the following components: 2 ng template DNA; 1× PCR buffer; 200 mM each deoxynucleotide triphosphate; 2.5 units AmpliTaq DNA polymerase (Perkin Elmer, U.S.A.); and, 13 pmol of each primer. The reaction mixture was heated to 94° C. for 7 min, and then was amplified using 33 cycles of: 94° C., 1 min; 55° C., 2 min; and, 72° C., 3 min. This was followed by final extension at 72° C. for 7 min.

A 1.1 kb PCS product was amplified. The fragment was separated on a 1.2% agarose gel and was purified by using GeneClean purification kit (BiolOl, U.S.A.). The purified fragment was digested with BsaI and BamHI, and was ligated into NcoI and BamHI-digested plasmid pTrc99A, which contains a strong inducible trcpromoter (see: Amann, E., et al., Gene, 25:167–168, 1983), so that the entire ompC gene including the signal sequence was inserted into the pTrc99A, right downstream of the trc promoter, to give pTrcC (see: FIG. 1). Then, the ligation mixture was transformed into E. coli XL1-Blue by electroporation. Transformants containing pTrcC recombinant plasmid were screened on LB plate containing 50 μg/L ampicillin. FIG. 1 shows a genetic map of a pTrcC recombinant plasmid.

The plasmid pTrcC was desinged to allow expression of the cell surface anchoring motif OmpC by a strong inducible trc promoter, and the point of inserting foreign peptides for cell surface display was aimed to be the PstI restriction site located in seventh external loop of OmpC. However, the pTrcC contains another PstI restriction site within the multiple cloning site on the plasmid, which makes it inconvenient to insert genes encoding foreign peptides/proteins of interest.

Figure 2:
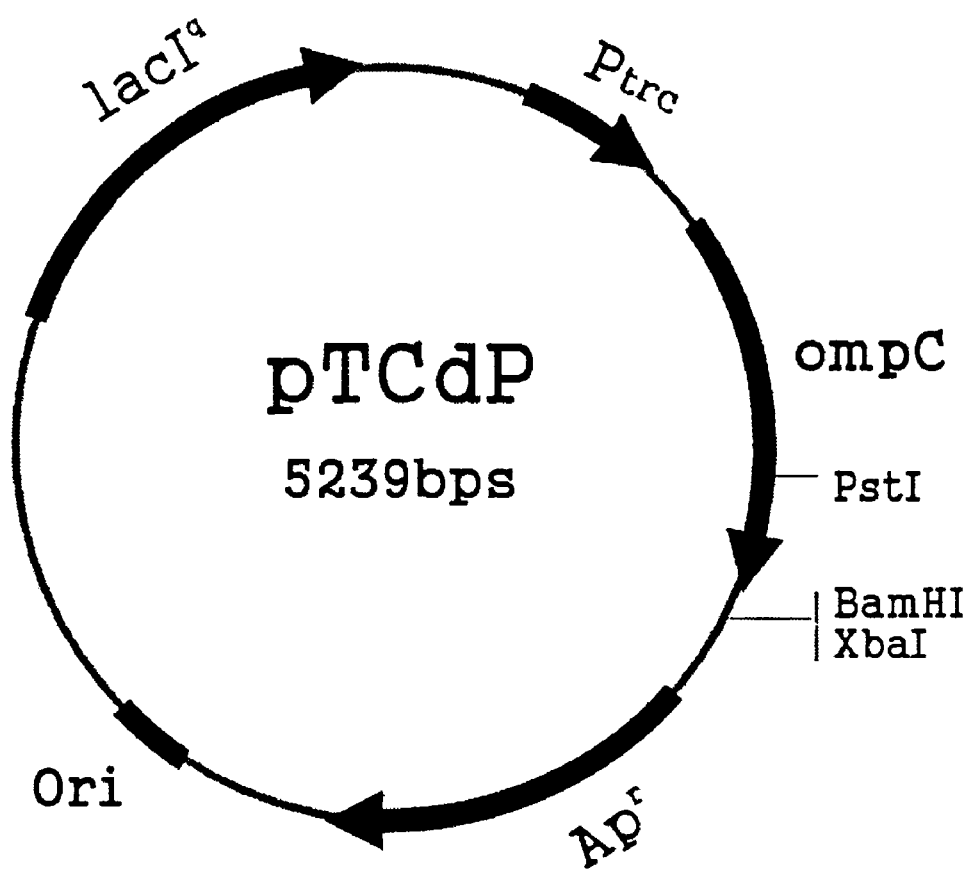
FIG. 2 shows a genetic map of plasmid pTCdP.

In order to delete unnecessary PstI restriction site present in the multiple cloning site, the pTrcC recombinant plasmid was digested with XbaI and HindIII, and cohesive ends of the plasmid after restriction endonuclease treatments were made blunt by using DNA polymerase I. T4 DNA ligation was followed, and the ligation mixture was used to transform E. coli XL1-Blue by electroporation. Transformants containing an expression vector pTCdP were screened on LB plate containing 50 μg/L ampicillin (see: FIG. 2). FIG. 2 shows a genetic map of a pTCdP recombinant expression vector. The expression vector pTCdP was introduced into E. coli MC4100. Transformant thus prepared was designated as 'Escherichia coli MC4100/pTCdP', and deposited with the Korean Collection for Type Cultures (KCTC, #52, Oun-dong, Yusong-ku, Taejon 305–333, Republic of Korea), an international depository authority as accession No. KCTC 0576BP on Feb. 3, 1999.

EXAMPLE 2
Construction of Recombinant Plasmid pTCHP1, pTCHP2, pTCHP3, pTCHP6 and pTCHP12

In order to test OmpC as an anchoring motif for the display of foreign peptides/proteins on the surface of E. coli, poly-histidine ("poly-His") peptide was selected as a model foreign peptide. Expression vectors that contain genes of varying copies of poly-His linkers were constructed. PCR was performed to obtain the gene encoding poly-His linker which is composed of 6 histidine residues. Two primers used in the reaction were 5'-GATAGATATCCTGCACGTCGACCCAAGCGGACA-TCACCATCATCACCAT-3' (SEQ ID NO:3) containing a PstI site(underlined) and 5'-CCAACTGCAGGATATCCTCGAGACCAGAATGGT-GATGATGGTGATG-3' (SEQ ID NO:4) containing a PstI site(underlined). The reaction mixture was heated to 94° C. for 5 min, and then was amplified using 10 cycles of: 94° C., 30 sec; 56° C., 30 sec; and, 72° C., 30 sec, followed by 20 cycles of: 94° C., 30 sec; 68° C., 30 sec; and, 72° C., 30 sec. The final extension was carried out at 72° C. for 7 min.

Figure 3:
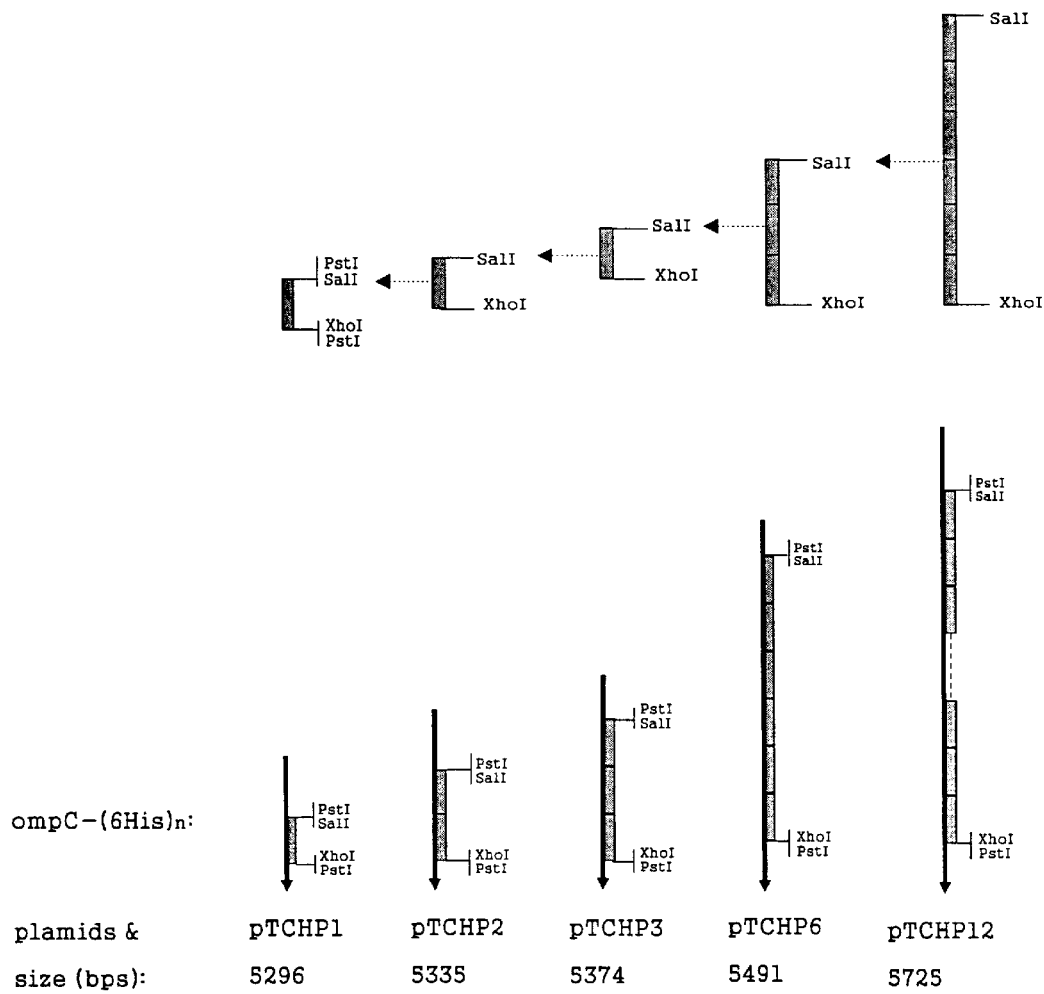
FIG. 3 shows genetic maps of plasmids pTCHP1, pTCHP2, pTCHP3, pTCBP6 and pTCHP12, and amino acid sequences of poly-histidine linker peptides each of which is inserted into the plasmids. Linker OmpC-(6His)$_1$ is SEQ ID NO:9, OmpC-(6His)$_2$ is SEQ ID NO:10, OmpC-(6His)$_3$ is SEQ ID NO: 1, OmpC-(6His)$_6$ is SEQ ID NO:12, and OmpC-(6His)$_{12}$ is SEQ ID NO:13.

A 77 bp of PCR product obtained was separated on a 1.2% agarose gel and was purified by using GeneClean kit (Bio101, U.S.A.). The purified DNA fragment contains a gene of poly-His linker peptide, PstI and SalI restriction sites at the 5'-terminus and XhoI and PstI restriction sites at the 3'-terminus. The PCR amplified DNA fragment and the recombinant expression vector pTCdP prepared in Example 1 were digested with PstI, and were ligated using T4 DNA ligase to construct an expression vector pTCHP1 (see: FIG. 3). The ligation mixture was transformed into E. coli XL1-Blue by electroporation, and transformants containing pTCHP1 recombinant plasmid were screened on LB plate containing 50 μg/L ampicillin. The plasmidpTCHP1 contains a gene encoding 1 set of poly-His linker peptide that is composed of 6 histidine residues.

In order to construct pTCHP2 recombinant plasmid which contains 2 sets of poly-His linker peptide, PCR product of 77 bp was digested with restriction enzymes SalI and XhoI, and the pTCHP1 recombinant plasmid was digested with SalI. The enzyme digested-PCR product and pTCHP1 recombinant plasmid were ligated, and the ligation mixture was introduced into E. coli XL1-Blue by electoporation. Transformants were slected on LB plate containing 50 μg/L ampicillin, and the recombinant pTCHP2 plasmid which contains 2 sets of poly-His linker peptide was isolated (see: FIG. 3).

pTCHP3, pTCHP6 and pTCHP12 were constructed in a similar manner as above. They contain gene of 3 sets, 6 sets and 12 sets of poly-His linker peptides, respectively. FIG. 3 shows the genetic maps of pTCHP$_n$ series expression vectors harboring different OmpC-(6His)$_n$ fusion genes, i.e., pTCHP1, pTCHP2, pTCHP3 pTCHP6 and pTCHP12, each of which contains one, two, three, six and twelve sets of 6His linkers, respectively. Among them, the expression vector pTCHP6 was introduced into E. coli MC4100 by electroporation. Transformant thus prepared was designated as 'Escherichia coli MC4100/pTCHP6', and deposited with the Korean Collection for Type Cultures (KCTC, #52, Oun-dong, Yusong-ku, Taejon 305–333, Republic of Korea), an international depository authority as accession No. KCTC 0577BP on Feb. 3, 1999.

EXAMPLE 3
Construction of Recombinant Plasmids pKCdP, pKCH3, pKCH6, and pKCH12

PCR was performed to clone lac promoter from plasmid pUC19 (see: Yanisch-Perron, C., et al., Gene, 33:103–119, 1985). Two primers used in the reaction were 5'-GGAATTCCATATGTGTTTCCTGTGTGAAATTGTT-3' (SEQ ID NO:5) and 5'-TGCTCACATGTTCTTTCCTG-3' (SEQ ID NO:6), and the reaction mixture was heated to 94° C. for 5 min, and then was amplified using 30 cycles of: 94° C., 50 sec; 54° C., 50 sec; and, 72° C., 70 sec. The final extension was carried out at 72° C. for 7 min.

A 357 bp of PCR product was obtained. The fragment was resolved on a 1.2% agarose gel and was purified by using GeneClean kit (Bio101, U.S.A.). The purified DNA fragment contains a lac promoter, AflIII restriction site at the 5'-terminus and NdeI restriction site at the 3'-terminus. The DNA fragment and the plasmid pET-3a (see: Conner G. E. and Udey J. A., DNA Cell Biol., 9:1–9, 1990) were digested with AflIII and NdeI, and the ligation was performed using T4 DNA ligase to construct vector pJHlac. The ligation mixture was transformed into E. coli XL1-Blue by electroporation, and transformants containing the resulting plasmid pJHlac were screened on LB plate containing 50 μg/L ampicillin.

Another PCR was performed to clone aminoglycoside 3'-phosphotransferase (Km$^r$) gene from plasmid pACYC177

(see: Rose, R. E., Nucl. Acids. Res., 16:356, 1988). Two primers used in the reaction were 5'-GCGGTACCTTTAAAGCCACGTTGTGTCTCAAA-3' (SEQ ID NO:7) and 5'-CGAATTCTTAGAAAAACTCATCGAGCA-3' (SEQ ID NO:8), and the reaction mixture was heated to 94° C. for 5 min, and then was amplified using 10 cycles of: 94° C., 50 sec; 55° C., 50 sec; and, 72° C., 70 sec, followed by 20 cycles of: 94° C., 50 sec; 63° C., 50 sec; and, 72° C., 70 sec. The final extension was carried out at 72° C. for 7 min.

A 944 bp of PCR product obtained was separated on a 0.7% agarose gel and was purified by using GeneClean kit. The purified DNA fragment contains a gene of aminoglycoside 3'-phosphotransferase (Km$^r$), KpnI and DraI restriction sites on the 5'-terminus and EcoRI restriction site on the 3'-terminus. This purifed DNA fragment and the plasmid pJHlac prepared as mentioned above were fully digested with DraI and EcoRI, and the ligation was performed using T4 DNA ligase to construct vector pJHlacK. The ligation mixture was transformed into E. coli XL1-Blue by electroporation, and transformants containing pJHlacK were screened on LB plate containing 30 μg/L kanamycin.

Figure 4:
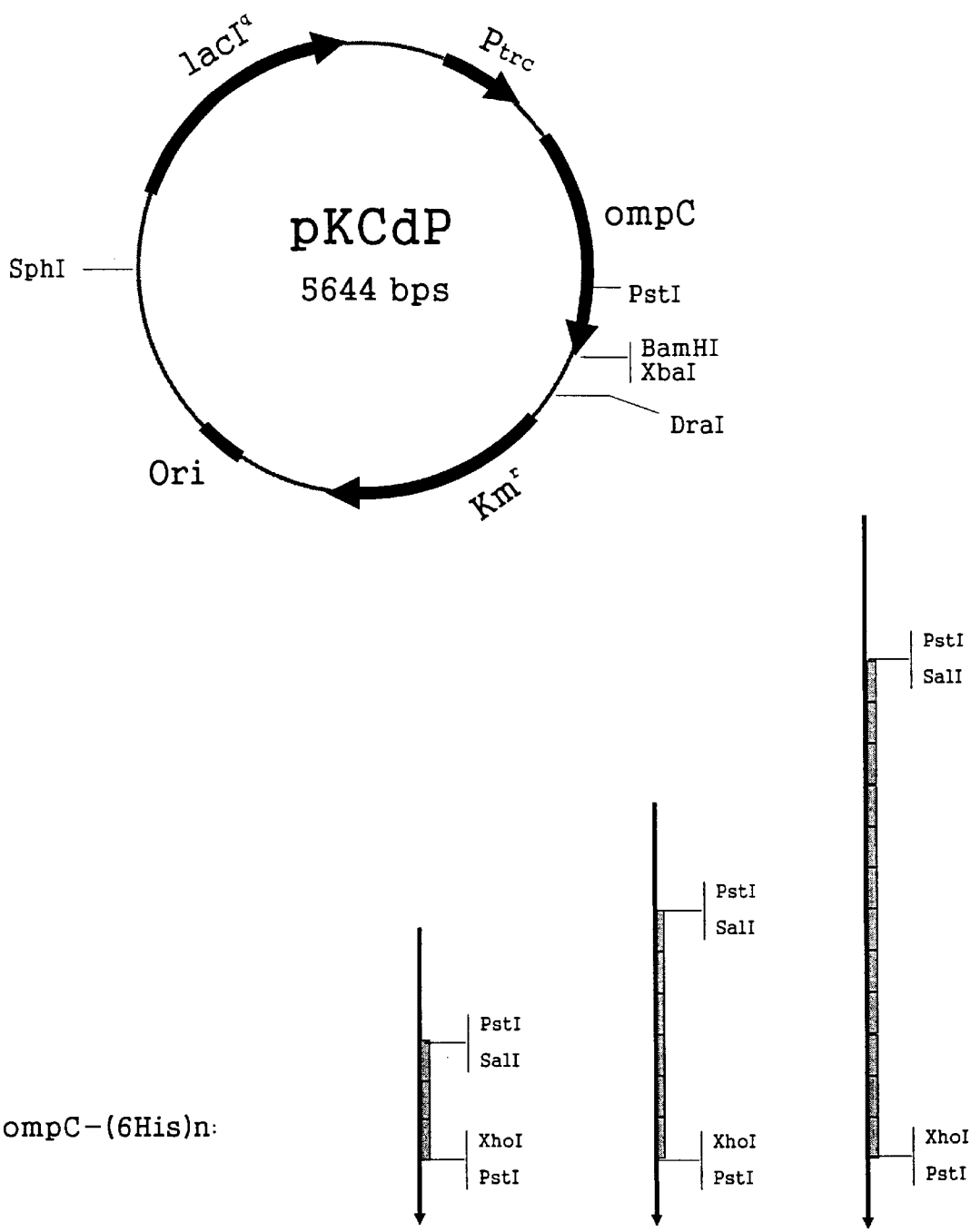
FIG. 4 shows genetic maps of plasmids pKCdp, pKCH3, pKCH6, and pKCH12.

Plasmid pJHlacK was double digested with EcoRV (partially) and DraI (fully), and the 1.4 kb of fragment containing Kmr gene was isolated on a 0.7% agarose gel and was purified by using GeneClean kit. The purified fragment and plasmid pTrc99A (see: Amann, E., et al., Gene, 25:167–168, 1983) fully digested with DraI were ligated using T4 DNA ligase to construct vector pTrcKm. The ligation mixture was transformed into E. coli XL1-Blue by electroporation, and transformants containing pTrcKm were screened on LB plate containing 30 μg/L kanamycin. Plasmid pTrcKm was then fully double-digested with SphI and DraI; and, so did pTCdP. The resulting 2.3 kb fragment of pTrcKm containing Kmr gene was ligated with the 3.4 kb fragment of pTCdP containing ompC gene using T4 ligase to construct pKCdP (see: FIG. 4). The ligation mixture was transformed into E. coli XL1-Blue by electroporation, and transformants were screened on LB plate containing 30 μg/L kanamycin. Plasmids pKCH3, pKCH6, and pKCH12 were also constructed by cloning the 3, 6 and 12 sets of poly(His) into the pKCdP in a similar way to construct pTCHPn series of vectors (see: FIG. 4). Among them, the expression vector pKCH6 was introduced into E. coli MC4100 by electroporation. Transformant thus prepared was designated as 'Escherichia coli MC4100/pKCH6', and deposited with the Korean Collection for Type Cultures (KCTC, #52, Oundong, Yusong-ku, Taejon 305–333, Republic of Korea), an international depository authority as accession No. KCTC 0653 BP on Aug. 17, 1999.

EXAMPLE 4
Expression of OmpC-(6His)$_n$ Fusion Proteins

To examine the expression of E. coli OmpC-(6His)$_n$ fusion proteins, E. coli MC4100 was transformed with expression vectors pTCHP1, pTCHP2, pTCHP3, pTCHP6 and pTCHP12, respectively. The expression of the OmpC-(6His)$_n$ fusion proteins was analysed on sodiumdodecylsulfate-polyacrylamide gel(SDS-PAGE). Recombinant E. coli MC4100 harboring the above recombinant expression vectors were inoculated into 50 ml of LB medium containing 50 μg/L ampicillin and were grown at 30° C. Because the ompC gene was inserted at the downstream of the trc promoter, the expression of ompC and its derivatives carrying (6His)$_n$ can be induced by adding IPTG. For the induction of E. coli MC4100 harboring pTCHP1, pTCHP2, pTCHP3, and pTCHP6, 0.01 mM IPTG was used. On the other hand, for the induction of E. coli MC4100 harboring pTCHP12, 0.1 mM. IPTG was used. A higher IPTG concentration was used for pTCHP12, because there was no expression of fusion protein when induced with 0.01 mM IPTG. IPTG was added when cell density reached the optical density at 600 nm (OD$_{600}$) of 0.6.

Samples of outer membrane fraction were collected from the culture of recombinant cells after 2 hours of the IPTG induction as follows: 3 ml of cell culture was centrifuged at 3,500×g for 5 min at 4° C., and the pellet was washed with 1 ml of 10 mM Na$_2$HPO$_4$ (pH 7.2) buffer, followed by centrifugation at 3,500×g for 5 min at 4° C. The pellet was resuspended in 0.5 ml of 10 mM Na$_2$HPO$_4$(pH 7.2) buffer, and the resuspended solution was sonicated thoroughly to disrupt cells. Cell debris-free supernatant was obtained by centrifugation of sonicated samples at 12,000×g for 2 min at room temperature. Total membrane protein fraction of the sample was isolated after centrifuging at 12,000×g for 30 min at 4° C. and resuspending the pellet in 0.5 ml of 0.5% (w/v) sarcosyl/10 mM Na$_2$HPO$_4$(pH 7.2) solution. The total outer membrane protein fraction was incubated on ice for 30 min, and insoluble fraction was obtained from the outer membrane protein fraction bycentrifugation at 12,000×g for 30 min at 4° C. The insoluble fraction was washed with 10 mM Na$_2$HPO$_4$ (pH 7.2) buffer, and was resuspended in 50 μl of PBS (0.274M NaCl, 0.041M Na$_2$HPO$_4$, 0.047M KH$_2$PO$_4$ and 0.005M KCl, pH 7.4) to obtain the solution of outer membrane protein fraction (see: Puenete, J. L., et al., Gene, 156:1–9, 1995).

Figure 5A:
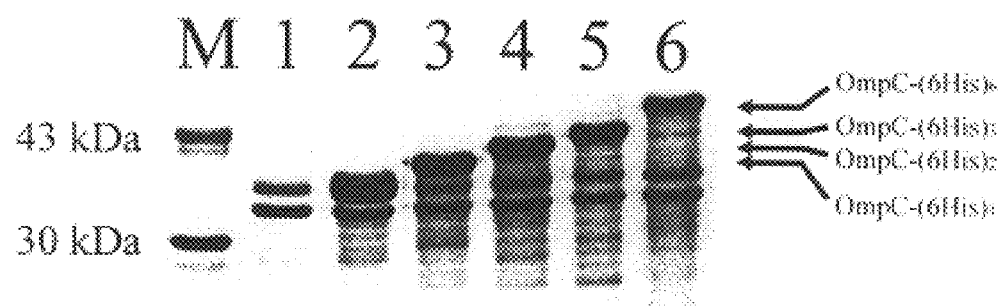
FIG. 5A is a photograph of SDS-PAGE showing the profile of the outer membrane protein fraction of recombinant microorganisms transformed with recombinant plasmid pTCHdP, pTCHP1, pTCHP2, pTCHP3 or pTCHP6.
Figure 5B:
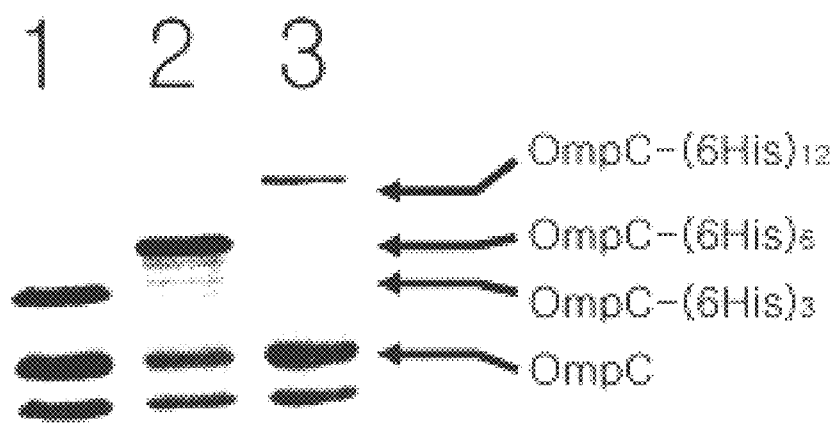
FIG. 5B is a photograph of SDS-PAGE showing the profile of the outer membrane protein fraction of recombinant microorganisms transformed with recombinant plasmid pTCHP3, pTCHP6 or pTCHP12.

Outer membrane protein fraction samples were analysed by electrophoresis on a 12% (w/v) SDS-PAGE as follows: 50 μl of each outer membrane protein fraction was mixed with 12 μl of SDS-PAGE sample buffer (60 mM Tris-HCl, 25% glycerol, 2% SDS, 14.4 mM 2-mercaptoethanol, and 0.1% bromophenol blue), and boiled for 10 min. The samples were loaded onto the 12% (w/v) polyacrylamide gel to perform the SDS-PAGE, and the gel was stained with Coomassie brilliant blue after electrophoresis. FIGS. 5(A) and 5(B) show the SDS-PAGE profiles of OmpC-(6His)$_n$ fusion proteins in E. coli MC4100. In FIG. 5A, M indicates the molecular weight standard (43kDa and 30 kDa from the top); lane 1 corresponds to outer membrane protein fraction from the E. coli MC4100; lane 2, from MC4100/pTCdP; lane 3, from MC4100/pTCHP1; lane 4, from MC4100/pTCHP2; lane 5, from MC4100/pTCHP3; and, lane 6, from MC4100/pTCHP6, respectively. In FIG. 5B, lane 1 corresponds to outer membrane protein fraction from the E. coli MC4100/pTCHP3; lane 2, from MC4100/pTCHP6; and, lane 3, from MC4100/pTCHP12. Each arrow indicates the relative size of OmpC-(6His)$_n$.

As can be seen in FIGS. 5(A) and 5(B), the apparent molecular mass of OmpC-(6His)$_n$ increased in proportion to n. Accordingly, it was demonstrated that the expressed IS OmpC-(6His)$_n$ fusion proteins were targeted to the E. coli outer membrane by OmpC protein. Besides, the result of ISDS-PAGE clearly demonstrated that the percentage of the fusion protein among the outer membrane proteins was high enough to reach over 30% of total outer membrane proteins when the gel was analysed with gel densitometer.

EXAMPLE 5
Whole Cell Adhesion to Ni-NTA-Agarose Beads

In order to investigate whether the poly-His peptide was properly expressed and located in the outer membrane of the E. coli, adhesion of recombinant E. coli cells to Nickel-nitrotriacetic acid (Ni-NTA)-agarose (Qiagen GmbH, Hilden, Germany) beads was examined. Because histidine is a good chelator for divalent metal ions, such as $Cd^{2+}$, $Cu^{2+}$, $Zn^{2+}$, $Ni^{2+}$ and $Pb^{2+}$, recombinant E. coli expressing poly- His peptide on its surface can adhere to $Ni^{2+}$ ion of the Ni-NTA-agarose beads.

Figure 6A:
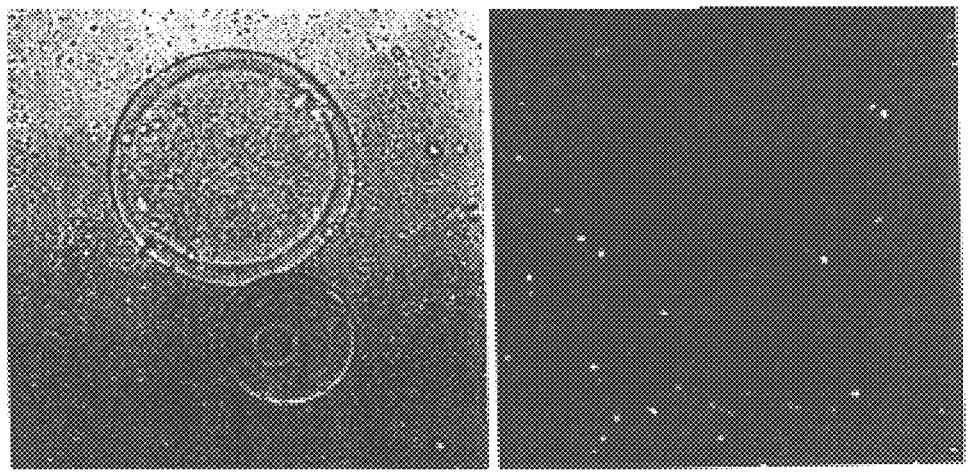
FIG. 6A is a transmission micrograph (left) and amatching fluorescent micrograph (right) showing the extent of recombinant whole cells transformed with pTCdP adhering to Ni-NTA-agarose beads.
Figure 6B:
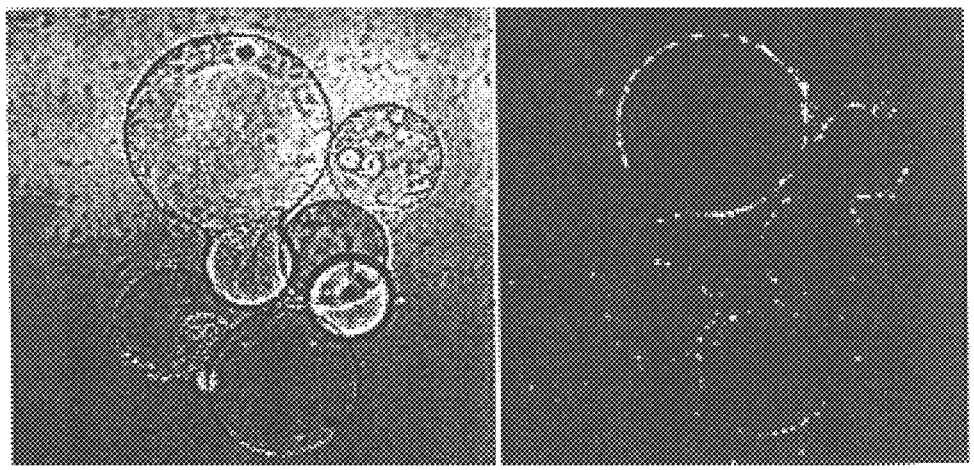
FIG. 6B is a transmission micrograph (left) and a matching fluorescent micrograph (right) showing the extent of recombinant whole cells transformed with pTCHP6 adhering to Ni-NTA-agarose beads.

Recombinant *E. coli* transformed with expression vectors pTCHP, and control expression vector pTCdP were cultured, and the OmpC-(6His)$_n$ fusion protein expression was induced with IPTG as described in Example 4. Two hours after the induction, 1 ml of induced cells were collected, centrifuged at 3,500×g for 5 min at 4° C., washed once with 0.85% (w/v) NaCl, resuspended in 0.5 ml of 0.85% (w/v) NaCl, and were mixed gently with Ni-NTA-agarose beads which were rewashed with 0.85% (w/v) NaCl. The cell-bead mixture was stained with 2 µg/ml of propidium iodide and observed under a laser scanning confocal microscopy (Carl Zeiss LSM 410, Oberkochen, Germany) Samples were excited by a 543 nm Helium/Neon laser, and the images were filtered by a longpass 570 nm filter. FIGS. 6(A) and 6(B) show the recombinant *E. coli* cells expressing OmpC-(6His)$_n$ fusion proteins bound to the Ni-NTA-agarose beads. Cells did not bind to the beads in case of cells harboring the negative-control expression vector pTCdP, and therefore, the beads were invisible under a fluorescent field (see: FIG. 6A). For the cells expressing OmpC-(6His)$_n$ fusion proteins, the outlines of the beads are clearly visible due to the attached recombinant *E. coli* cells (see: FIG. 6B). Since only the exposed (6His), are accessible to nickel ions on the agarose beads, these micrographs indicate that (6His)$_n$ peptides are successfully exposed outside the cell.

EXAMPLE 6
Heavy Metal Adsorption by *E. coli* Cells Displaying OmpC-(6His)$_n$ Fusion Proteins Recombinant *E. coli* expressing OmpC-(6His)$_n$ fusion proteins were examined for their abilities to adsorb $Cd^{2+}$: Induced cells were washed twice with 0.85% (w/v) NaCl, and were resuspended in 0.85% (w/v) NaCl (pH 5.8) to reach a final concentration of $ODE_{600}$=5.0. An equal volume of $CdCl_2$ (50 ppm in 0.85% (w/v) NaCl, pH 5.8) was added, and the mixture was incubated for 24 h at 25° C. with shaking. Cells were pelleted, washed twice with 0.85% (w/v) NaCl, and then were digested with 70% (w/v) nitric acid overnight at room temperature. Samples were analysed by Atomic Analysis System (Perkin-Elmer 3100, U.S.A.) using an air-acetylene flame and a hollow cathode lamp. The wavelength and slit width were 228.8 nm and 0.7 nm, respectively.

Figure 7A:
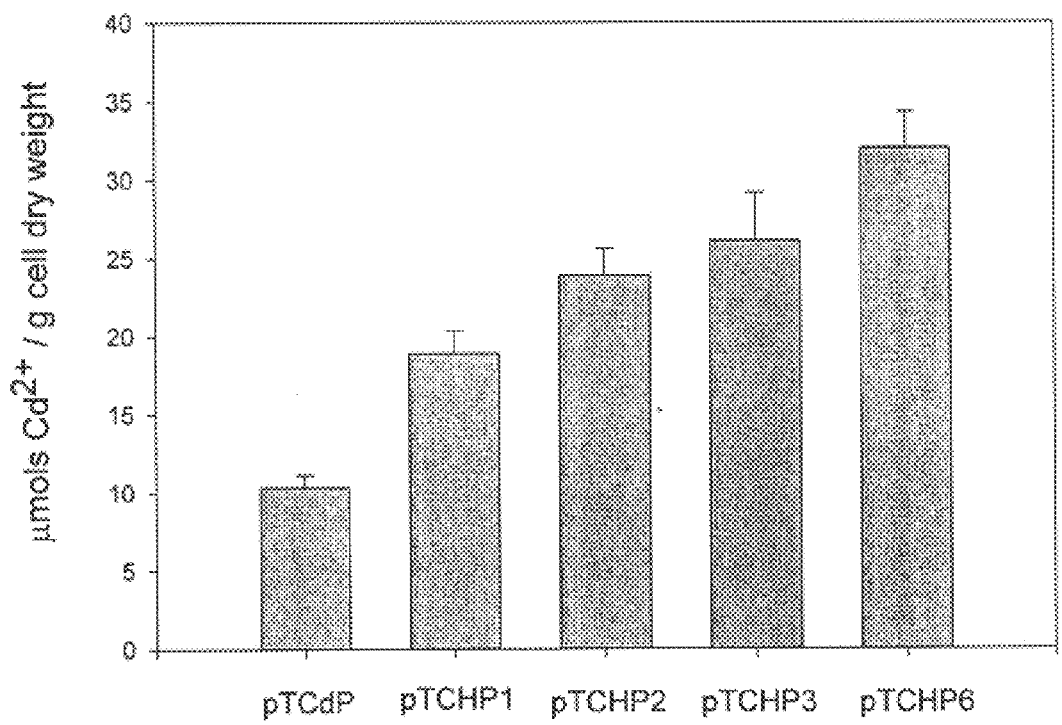
FIG. 7A is a graph showing the extent of $Cd^{2+}$ accumulation by recombinant *E. coli* strains transformed with recombinant plasmid pTCdP, pTCHP1, pTCHP2, pTCHP3 or pTCHP6.

As can be seen in FIG. 7A, cells harboring pTCHP1, pTCHP2, pTCHP3 and pTCHP6 could absorb 18.9, 23.9, 26.1 and 32.0 µmol of $Cd^{2+}$ per grams of cell dry weight, respectively, while control cells harboring pTCdP could absorb 10.3 µmol/g. This result clearly demonstrated that: the $Cd^{2+}$ removal capacity increases as the number of poly-His units on the cell surface increases. Besides, the $Cd^{2+}$ removal capacity of poly-His clusters displayed using OmpC as an anchoring motif was 32 µmol per gram cell dry weight, which was twice higher than that obtained by poly-His displayed using LamB as the anchoring motif (see: Sousa, C., et al., Nature Biotechnol., 14:1017–1020, 1996).

Figure 7B:
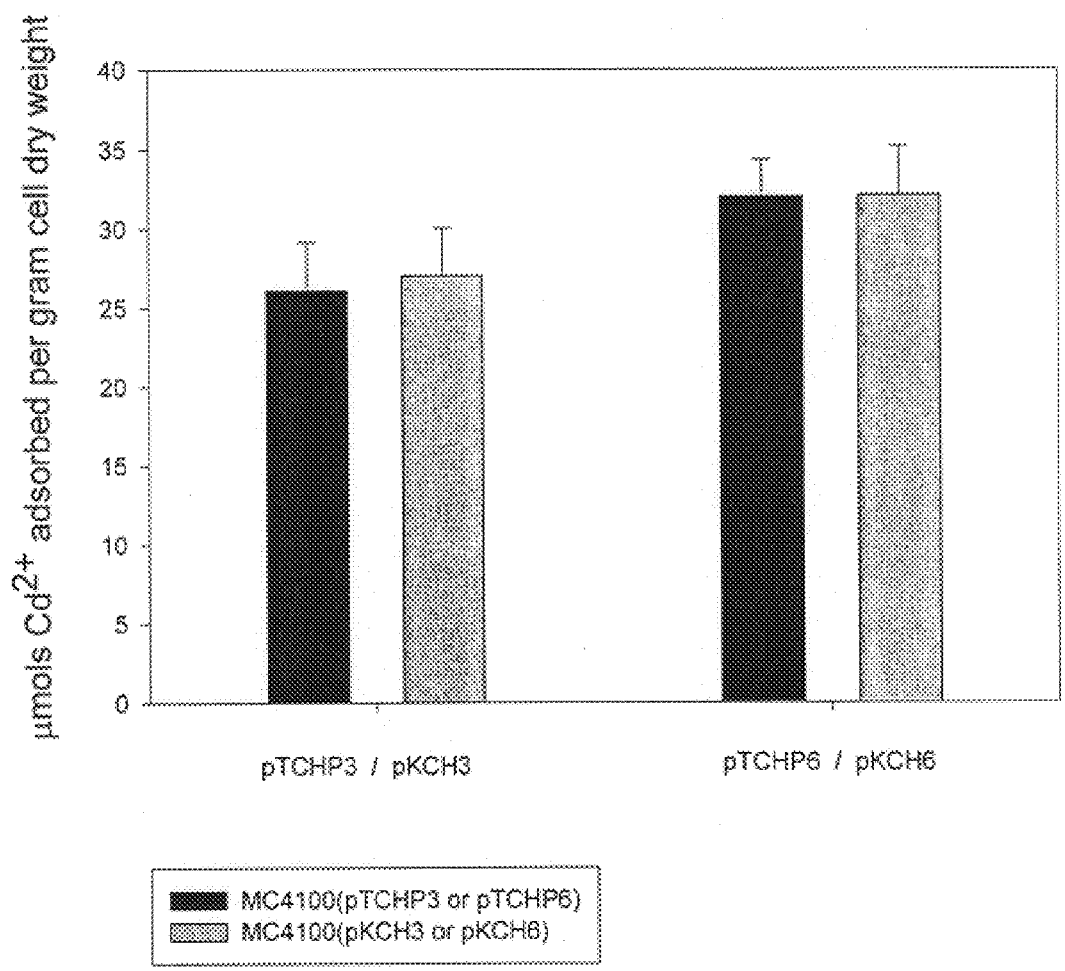
FIG. 7B is a graph showing the comparison of $Cd^{2+}$ accumulation by recombinant *E. coli* strains transformed with recombinant plasmid pTCHP3, pTCHP6, pKCH3 or pKCH6.

As can be seen in FIG. 7B, cells harboring pKCH3 and pKCH6 could absorb 27.0 and 32.1 µmol of $Cd^{2+}$ per grams of cell dry weight, respectively, matching the $Cd^{2+}$ removal ability of cells harboring Apr vectors.

EXAMPLE 7
Comparison of Cultivation Properties of MC4100 (pTCHP$_n$) and MC4100 (pKCH$_n$)

Recombinant *E. coli* transformed with pTCHP3, pTCHP6, pKCH3, and pKCH6 were compared for their growth characteristcs: Strains were cultivated at 30° C. in LB medium supplemented with 50 µg/ml of ampicillin or 30 µg/ml of kanamycin. Cells were induced at the $OD_{600}$ of 0.6 by adding IPTG to the final concentration of 10 µM for strains harboring pTCFIP3 and pTCHP6, and to 100 µM for strains harboring pKCH3 and pKCH6, and were grown for 2 more hours. Cell growth was monitored by measuring the absorbance at 600 nm ($OD_{600}$).

Figure 8:
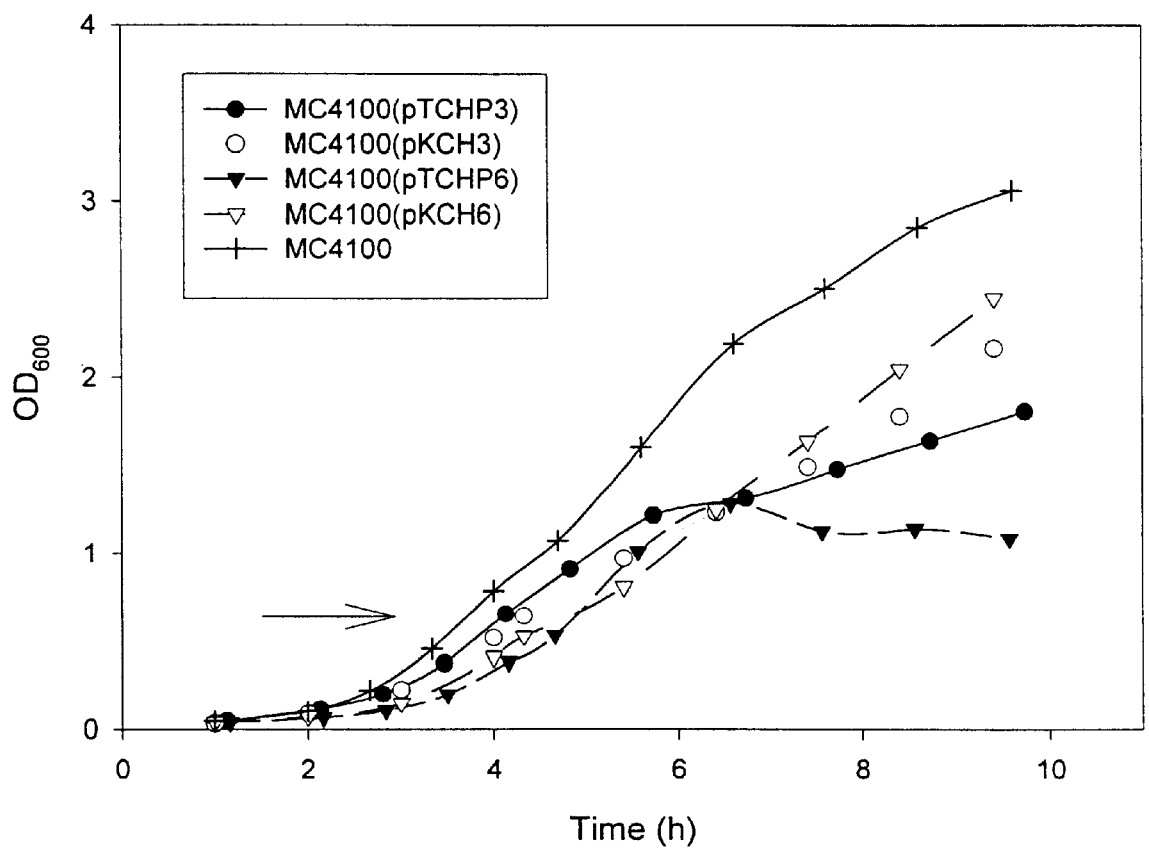
FIG. 8 is a graph showing the growth characteristics of recombinant *E. coli* strains transformed with a recombinant plasmid pTCHP3, pTCHP6, pKCH3 or pKCH6.

As can be seen in FIG. 8, the final cell density of MC4100(pKCH3) and MC4100(pKCH6) were much higher than that of MC4100(pTCHP3) and MC4100(pTCHP6). Therefore, if better cell growth is required for certain applications (e.g., high cell density cultivations), pKCH$_n$ series vectors are more useful.

As clearly illustrated and demonstrated as above, the present invention provides novel expression vectors comprising the OmpC gene from *E. coli* as a cell surface anchoring motif to express foreign protein on the cell surface, *E. coli* cells which are transformed with the said expression vectors, and a method for displaying foreign protein/peptide on the cell surface of microorganism. In addition, the present invention provides a heavy metal remover comprising a microorganism which is transformed with an expression vector containing a gene of poly-histidine linker peptide and a gene of OmpC derived from *E. coli*.

A variety of applications are possible by inserting appropriate foreign gene into the recombinant expression vector of the present invention. The unlimited applications include live vaccine development, peptide libraries screening, antibody production, environmental bioadsorbents, whole cell catalysis, and biosensor development.

---

What is claimed is:

1. An expression vector designed to express a foreign protein in fused form with an OmpC as a cell surface anchoring motif on the cell surface of a microorganism comprising: a gene encoding the entire *Escherichia coli* outer membrane protein C(OmpC) comprising a secretion signal and a targeting signal in which a gene of interest (GOI) is inserted into the 7$^{th}$ external loop.

2. The Expression vector of claim 1 further comprising an inducible promoter.

3. The Expression vector of claim 2 wherein the inducible promoter is Ptrc.

4. The Expression vector of claim 1 further comprising a selectable marker.

5. The expression vector of claim 4 wherein the selectable marker is β-lactamase (AP$^R$).

6. The expression vector of claim 4 wherein the selectable marker is aminoglycoside 3-phosphotrnnsferase (Km$^R$).

7. The expression vector of claim 1 wherein said GOI encodes poly-histidine.

8. The expression vector of claim 7 wherein said poly-histidine is a linker peptide composed of 6 or more histidine residues.

9. The expression vector of claim 8 wherein the poly-histidine linker peptide is composed of 2 or more repeats of a 6 histidine residue cluster.

10. The expression vector of claim 8 wherein the poly-histidine linker peptide is composed of 12 or more repeats of a 6 histidine residue cluster.

11. The expression vector of claim 1 wherein said expression vector comprises pTCdp.

12. The expression vector of claim 1 wherein said expression vector comprises pTCHP6.

13. The expression vector of claim 1 wherein said expression vector comprises KCH6(KCTC 0653BP (deposited as KCTC 0653BP).

14. A recombinant microorganism comprising the expression vector of claim 1.

15. The recombinant microorganism of claim 14 wherein said microorganism is *E. coli*.

16. The recombinant microorganism of claim 15 wherein said *E. coli* is MC4100.

17. The recombinant microorganism of claim 16 which is *E. coli* KCTC 0576BP.

18. The recombinant microorganism of claim 16 which is *E. coli* KCTC 0577BP.

19. The recombinant microorganism of claim 16 which is *E. coli* KCTC 0653BP.

20. A heavy metal remover which comprises a recombinant microorganism transformed with an expression vector comprising a gene encoding a poly-histidine linker peptide fused to the entire gene of *E. coli* outer membrane protein C(OmpC) as a cell surface anchoring motif.

21. The heavy metal remover of claim 20, wherein the microorganism is *Escherichia coli* MC4100/pTCHP6 (KCTC0577BP) or *Escherichia coli* MC4100/pKCH6 (KCTC0653BP).

22. A method for displaying a recombinant protein on the surface of a microorganism, which comprises the steps of:
1) providing the expression vector of claim 1 and transforming a microorganism with the expression vector; and
2) culturing the transformed microorganism to express the desired protein.

23. The method of claim 22, wherein the microorganism is *Escherichia coli*.

24. The method of claim 22 wherein the expression vector is pTCdP or pKCH6.

25. The method of claim 22 wherein the step of culturing the microorganism transformed with the expression vector to express the desired protein comprises induction with IPTG.

* * * * *

UNITED STATES PATENT AND TRADEMARK OFFICE
CERTIFICATE OF CORRECTION

PATENT NO.   : 6,274,345 B1                                                    Page 1 of 1
DATED        : August 14, 2001
INVENTOR(S)  : Sang Yup Lee, Zhaohui Xu and Jong Hyun Choi It is certified that error appears in the above-identified patent and that said Letters Patent is hereby corrected as shown below:

Column 18,
Line 62-63, "KCH6(KCTC 0653 BP (deposited as KCTC 0653 BP)." should be changed to -- pKCH6. --.

Signed and Sealed this

Fourth Day of June, 2002

*Attest:*

*Attesting Officer*

JAMES E. ROGAN
*Director of the United States Patent and Trademark Office*

SEQUENCE LISTING

<160> NUMBER OF SEQ ID NOS: 13

<210> SEQ ID NO 1
<211> LENGTH: 34
<212> TYPE: DNA
<213> ORGANISM: Artificial Sequence
<220> FEATURE:
<223> OTHER INFORMATION: Single stranded oligonucleotide primer

<400> SEQUENCE: 1
ctgcgcctgg tctcacatga aagttaaagt actg        34

```
<210> SEQ ID NO 2
<211> LENGTH: 30
<212> TYPE: DNA
<213> ORGANISM: Artificial Sequence
<220> FEATURE:
<223> OTHER INFORMATION: Single stranded oligonucleotide primer

<400> SEQUENCE: 2
ccgggatcct tattagaact ggtaaaccag                                  30

<210> SEQ ID NO 3
<211> LENGTH: 49
<212> TYPE: DNA
<213> ORGANISM: Artificial Sequence
<220> FEATURE:
<223> OTHER INFORMATION: Single stranded olignucleotide primer

<400> SEQUENCE: 3
gatagatatc ctgcaggtcg acccaagcgg acatcaccat catcaccat            49

<210> SEQ ID NO 4
<211> LENGTH: 46
<212> TYPE: DNA
<213> ORGANISM: Artificial Sequence
<220> FEATURE:
<223> OTHER INFORMATION: Single stranded oligonucleotide primer

<400> SEQUENCE: 4
ccaactgcag gatatcctcg agaccagaat ggtgatgatg gtgatg                46

<210> SEQ ID NO 5
<211> LENGTH: 34
<212> TYPE: DNA
<213> ORGANISM: Artificial Sequence
<220> FEATURE:
<223> OTHER INFORMATION: Single stranded oligonucleotide primer

<400> SEQUENCE: 5
ggaattccat atgtgtttcc tgtgtgaaat tgtt                             34

<210> SEQ ID NO 6
<211> LENGTH: 20
<212> TYPE: DNA
<213> ORGANISM: Artificial Sequence
<220> FEATURE:
<223> OTHER INFORMATION: Single stranded oligonucleotide primer

<400> SEQUENCE: 6
tgctcacatg ttctttcctg                                             20

<210> SEQ ID NO 7
<211> LENGTH: 32
<212> TYPE: DNA
<213> ORGANISM: Artificial Sequence
<220> FEATURE:
<223> OTHER INFORMATION: Single stranded oligonucleotide primer

<400> SEQUENCE: 7
gcggtacctt taaagccacg ttgtgtctca aa                               32

<210> SEQ ID NO 8
<211> LENGTH: 27
<212> TYPE: DNA
<213> ORGANISM: Artificial Sequence
<220> FEATURE:
<223> OTHER INFORMATION: Single stranded oligonucleotide primer
```

<400> SEQUENCE: 8
cgaattctta gaaaaactca tcgagca        27

<210> SEQ ID NO 9
<211> LENGTH: 24
<212> TYPE: PRT
<213> ORGANISM: Artificial Sequence
<220> FEATURE:
<223> OTHER INFORMATION: Histidine linker.

<400> SEQUENCE: 9

Leu Gln Val Asp Pro Ser Gly His His His His His Ser Gly Leu
 1               5                  10                  15

Glu Asp Ile Leu Gln Ser Lys Gly
            20

<210> SEQ ID NO 10
<211> LENGTH: 37
<212> TYPE: PRT
<213> ORGANISM: Artificial Sequence
<220> FEATURE:
<223> OTHER INFORMATION: Histidine linker.

<400> SEQUENCE: 10

Leu Gln Val Asp Pro Ser Gly His His His His His Ser Gly Leu
 1               5                  10                  15

Asp Pro Ser Gly His His His His His Ser Gly Leu Glu Asp Ile
            20                  25                  30

Leu Gln Ser Lys Gly
        35

<210> SEQ ID NO 11
<211> LENGTH: 50
<212> TYPE: PRT
<213> ORGANISM: Artificial Sequence
<220> FEATURE:
<223> OTHER INFORMATION: Histidine linker.

<400> SEQUENCE: 11

Leu Gln Val Asp Pro Ser Gly His His His His His Ser Gly Leu
 1               5                  10                  15

Asp Pro Ser Gly His His His His His Ser Gly Leu Asp Pro Ser
            20                  25                  30

Gly His His His His His Ser Gly Leu Glu Asp Ile Leu Gln Ser
        35                  40                  45

Lys Gly
    50

<210> SEQ ID NO 12
<211> LENGTH: 89
<212> TYPE: PRT
<213> ORGANISM: Artificial Sequence
<220> FEATURE:
<223> OTHER INFORMATION: Histidine linker.

<400> SEQUENCE: 12

Leu Gln Val Asp Pro Ser Gly His His His His His Ser Gly Leu
 1               5                  10                  15

Asp Pro Ser Gly His His His His His Ser Gly Leu Asp Pro Ser
            20                  25                  30

Gly His His His His His His Ser Gly Leu Asp Pro Ser Gly His His

```
                    35                  40                  45

His His His His Ser Gly Leu Asp Pro Ser Gly His His His His
         50                  55                  60

His Ser Gly Leu Asp Pro Ser Gly His His His His His Ser Gly
65                  70                  75                  80

Leu Glu Asp Ile Leu Gln Ser Lys Gly
                85

<210> SEQ ID NO 13
<211> LENGTH: 167
<212> TYPE: PRT
<213> ORGANISM: Artificial Sequence
<220> FEATURE:
<223> OTHER INFORMATION: Histidine linker.

<400> SEQUENCE: 13

Leu Gln Val Asp Pro Ser Gly His His His His His Ser Gly Leu
1               5                   10                  15

Asp Pro Ser Gly His His His His His Ser Gly Leu Asp Pro Ser
                20                  25                  30

Gly His His His His His His Ser Gly Leu Asp Pro Ser Gly His His
            35                  40                  45

His His His His Ser Gly Leu Asp Pro Ser Gly His His His His
         50                  55                  60

His Ser Gly Leu Asp Pro Ser Gly His His His His His Ser Gly
65                  70                  75                  80

Leu Asp Pro Ser Gly His His His His His Ser Gly Leu Asp Pro
                85                  90                  95

Ser Gly His His His His His Ser Gly Leu Asp Pro Ser Gly His
            100                 105                 110

His His His His Ser Gly Leu Asp Pro Ser Gly His His His His
            115                 120                 125

His His Ser Gly Leu Asp Pro Ser Gly His His His His His Ser
         130                 135                 140

Gly Leu Asp Pro Ser Gly His His His His His Ser Gly Leu Glu
145                 150                 155                 160

Asp Ile Leu Gln Ser Lys Gly
                165
```